United States Patent [19]

Chlosta et al.

[11] Patent Number: 4,558,603
[45] Date of Patent: Dec. 17, 1985

[54] NEEDLE ASSEMBLY FOR INTRODUCING A CARRIER GAS INTO A SAMPLE VESSEL

[75] Inventors: Wolfgang Chlosta, Überlingen; Wolfgang Riegger, Salem, both of Fed. Rep. of Germany

[73] Assignee: Bodenseewerk Perkin-Elmer & Co., GmbH, Überlingen, Fed. Rep. of Germany

[21] Appl. No.: 553,673

[22] Filed: Nov. 21, 1983

[30] Foreign Application Priority Data

Jan. 22, 1983 [DE] Fed. Rep. of Germany ....... 3302158

[51] Int. Cl.⁴ ............................................ G01N 35/06
[52] U.S. Cl. ................................ 73/864.21; 73/864.24; 73/864.81; 73/864.85
[58] Field of Search ............ 73/864.21, 864.22, 864.23, 73/864.24, 864.81, 864.82, 864.85, 863.81; 863.85

[56] References Cited

U.S. PATENT DOCUMENTS

| | | | |
|---|---|---|---|
| 3,545,279 | 12/1970 | Jentzsch et al. | 73/863.81 |
| 3,730,002 | 5/1973 | Penton | 73/864.82 |
| 3,754,443 | 8/1973 | Harris, Sr. et al. | 73/864.21 X |
| 3,885,438 | 5/1975 | Harris, Sr. et al. | 73/863.81 |
| 4,094,195 | 6/1978 | Friswell et al. | 73/864.21 |
| 4,094,196 | 6/1978 | Friswell | 73/864.22 X |
| 4,117,727 | 10/1978 | Friswell et al. | 73/864.21 X |
| 4,199,988 | 4/1980 | Riegger | 73/863.81 |
| 4,237,733 | 12/1980 | Kolb et al. | 73/864.21 |
| 4,294,126 | 10/1981 | Tomoff et al. | 73/864.21 |
| 4,464,940 | 8/1984 | Pospisil | 73/864.81 X |

FOREIGN PATENT DOCUMENTS 1284660 12/1968 Fed. Rep. of Germany .
2815023 10/1979 Fed. Rep. of Germany .
2818251 11/1979 Fed. Rep. of Germany .

*Primary Examiner*—Richard L. Chiesa
*Attorney, Agent, or Firm*—E. T. Grimes; F. L. Masselle; J. D. Crane

[57] ABSTRACT

A needle is movable by a servomotor between a position of rest and an operating position in a stationary housing. The needle includes a tip and a first lateral opening close to the tip and a second lateral opening spaced therefrom. A longitudinal passage of the housing through which the needle is guided includes a pair of seals at the lower end and a seal at the upper end. A carrier gas conduit ends in the longitudinal passage axially inwards of the seals. A port communicating with atmosphere ends axially inwards of the upper seal. The arrangement permits a sample extraction from sample vessels closed by a membrane without the sample vessels having to be lifted and pressed against the needle.

17 Claims, 5 Drawing Figures

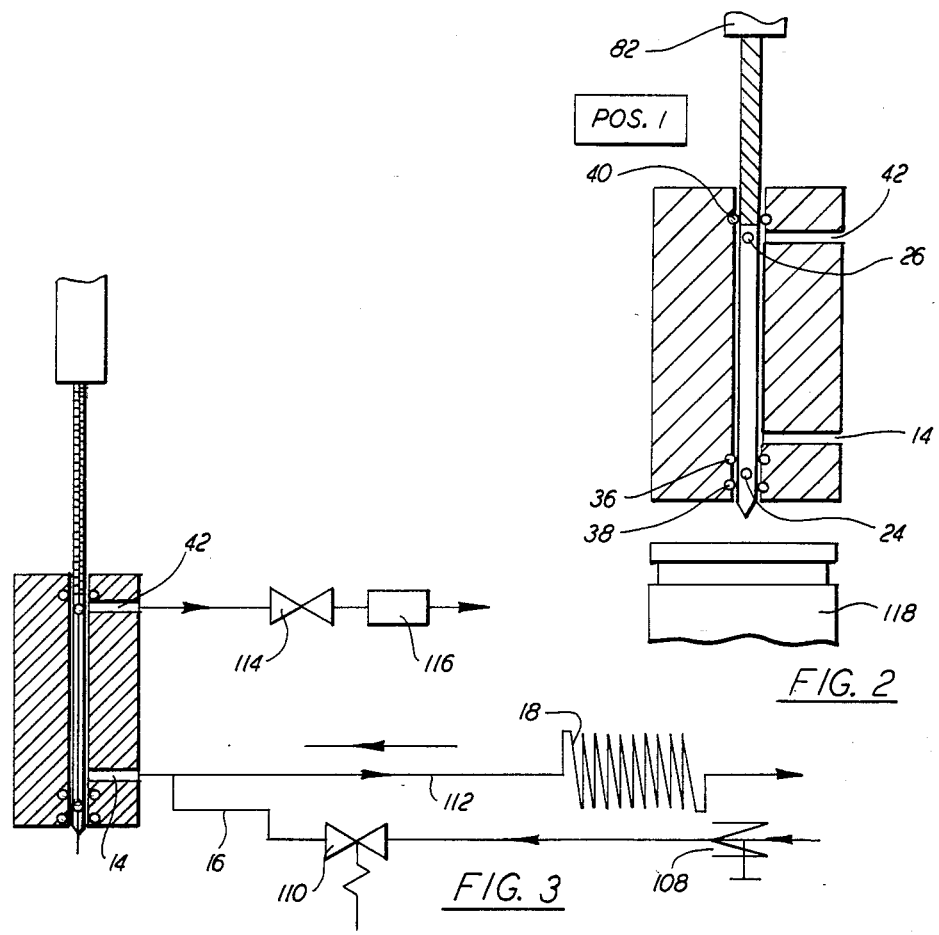

NEEDLE ASSEMBLY FOR INTRODUCING A CARRIER GAS INTO A SAMPLE VESSEL

BACKGROUND OF THE INVENTION

The present invention generally relates to a needle assembly for introducing a carrier gas into a sample vessel closed by a self-sealing membrane and, in particular, relates to an assembly useful as a sampling device in gas chromatography operating in accordance with the head space method.

A state of equilibrium in which the partial pressures of the sample components in the head space unambiguously depend on the composition of the sample is obtained in the head space above a sample liquid in a sample vessel closed by a membrane. With a sampling device operating in accordance with the head space method, the sample supplied to the separating column of a gas chromatograph is taken from this head space. For this purpose a needle is pierced through the self-sealing membrane. The needle is connected to the inlet of a dosing head of the gas chromatograph which is connected to a carrier gas conduit having a shutoff valve contained therein. Initially, carrier gas enters through the needle into the head space of the closed sample vessel with the shut-off valve open such that a carrier gas pressure builds up in the sample vessel. This does not change anything in the partial pressures of the sample components in the head space. When the shut-off valve is closed, the carrier gas pressure in the dosing head breaks down. Then a gas sample is pressed from the headspace into the closing head and the inlet of the separating column by the excess pressure in the sample vessel. After a well defined time, the shut-off valve is again opened whereby the dosing is terminated and the sample is transported into the separating column of the gas chromatograph (German Pat. No. 1 208 523).

To prevent the carrier gas from flowing unrestrictedly out of the needle after the needle has been removed from the sample vessel, it is known (German Pat. No. 1 284 660) to arrange the needle in a piston sealingly movable in a cylinder. The cylinder includes a restricting outlet and is closed on its end facing the sample vessel by a further self-sealing membrane. The cylinder is under the action of a compression spring which is supported on the piston and tends to push the cylinder over the needle. In the position of rest the needle with its opening being near the pointed end is in the interior of the cylinder.

In this known apparatus, the needle is stationary and always connected to the dosing head and the carrier gas conduit. The cylinder is longitudinally movably guided relative to the stationary needle. A sample vessel is placed with its self-sealing membrane into engagement with the end face of the cylinder closed by the further self-sealing membrane and is pushed upwards, the cylinder being pressed back thereby and the needle entering into the sample vessel through the two self-sealing membranes. In the position of rest, a rinsing flow flows through the needle, the rate of which flow is determined by the restriction of the outlet of the cylinder. The rinsing flow ensures that no vapors in the needle are carried over from one sample to the next.

By the German Offenlegungsschrift No. 28 15 023, a needle assembly is known in which the carrier gas is introduced into an apparatus-fixed housing and a needle is sealingly guided in sealing means in the housing for sliding movement between a position of rest and an operating position. The needle has a tip having a first lateral opening provided close to this tip. The needle has a second opening spaced from the first lateral opening. In the operating position of the needle, the second opening communicates with the chamber formed in the housing such that a carrier gas flows through the second opening into the needle and out of the first opening. When the sample vessel is pressed against the action of a return spring, the needle is longitudinally movably guided between a position of rest and an operating position. In the position of rest, the second opening is located in the chamber to which a restricted rinsing flow is supplied. This rinsing flow passes through the second lateral opening of the needle and emerges to atmosphere through the first lateral opening.

When the sample vessel is pressed on, the needle is pushed into its operating position directly or through a spring mechanism.

Conventional needle assemblies require the sample vessel to be lifted and pressed against the needle. Such mechanisms require considerable design expenditure, particularly when the sample vessels are arranged in a thermostatized turntable (German Pat. No. 1 297 904 or German Pat. No. 28 18 251).

SUMMARY OF THE INVENTION

Accordingly, one object of the present invention is to provide a needle assembly wherein the sample vessel is not pressed against the needle assembly.

This object is achieved, at least in part, by an assembly wherein the needle is moved, by means of a servomotor between a position of rest and an operating position, relative to a stationary housing. The housing includes a longitudinal passage, the wall of which surrounds the needle leaving a narrow annular gap, having a first end adjacent the tip of the needle and a second end remote therefrom, a sealing means includes a pair of seals in the area of the first end of the longitudinal passage axially spaced apart from each other and which closely engage the needle, and a seal in the area of the second end of the longitudinal passage and closely engaging the needle, the port for the carrier gas conduit ends at the first end axially inwards of the seals and the needle is movable under the control of the servomotor, from a rest position whereat the first lateral opening at the first end is located between the pair of seals and to an operating position whereat the needle with its tip and the first lateral opening at the first end extends out of the housing and the second lateral opening is arranged beside the port for the carrier gas conduit.

In the assembly, the needle is moved by a servomotor such that, in the operating position, it can be struck into the sample vessel remaining in its plane. That requires, however, that the carrier gas is introduced into the movable needle such that dead volumes, which may cause sample cross-contamination, are kept as small as possible. This is achieved by providing the housing with a narrow longitudinal passage and the sealing means.

Other objects and advantages will become apparent to those skilled in the art from the following detailed description read in conjunction with the appended claims and the drawing attached hereto.

BRIEF DESCRIPTION OF THE DRAWING

FIG. 2 is a partial cross-sectional side elevation of a needle and its support on the displacement member of a servomotor;

FIG. 3 is a schematic diagram of the needle assembly, the separating column and the carrier gas circuit;

FIG. 4 is a schematic diagram showing the different positions into which the needle is movable.

DETAILED DESCRIPTION OF THE INVENTION

Figure 1:
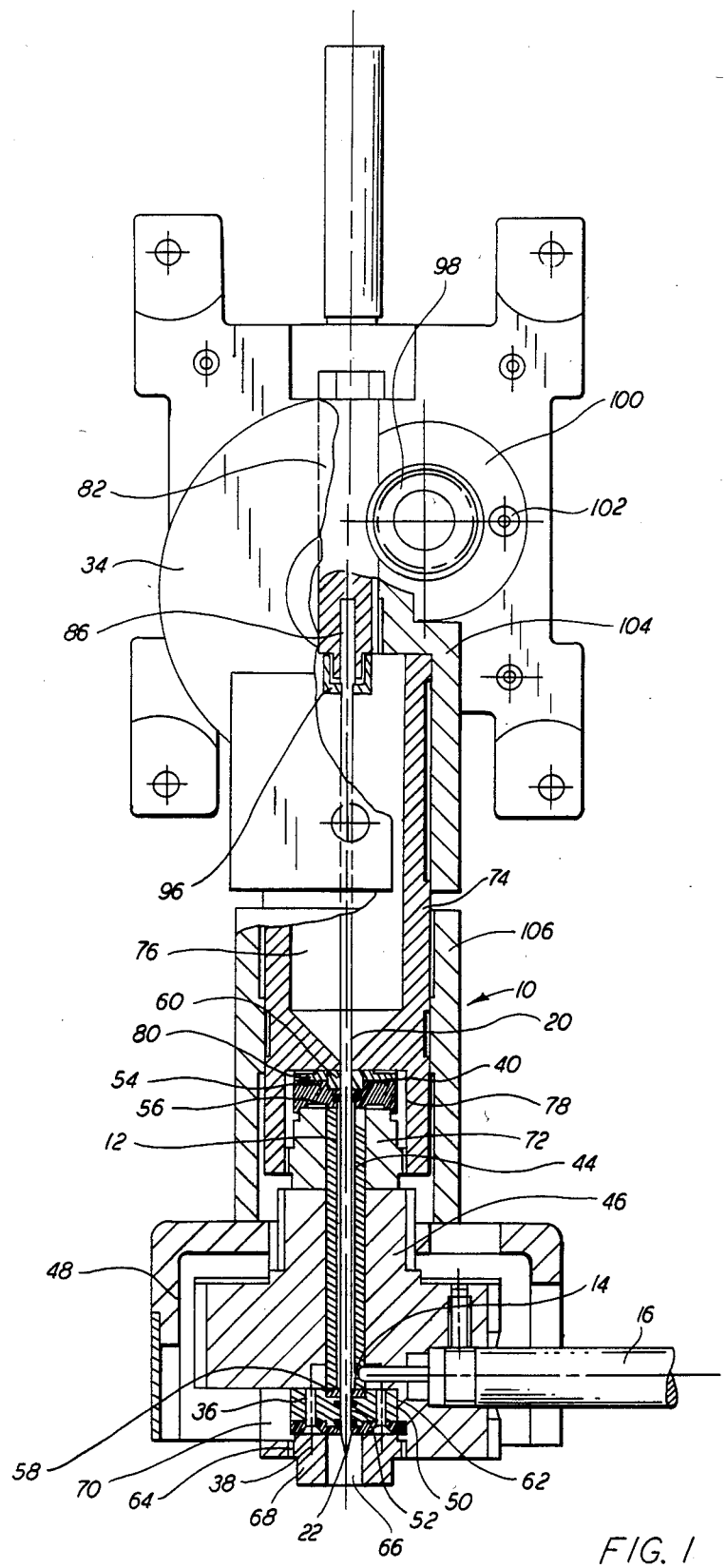
FIG. 1 is a partial cross-sectional side elevation of a needle assembly, not drawn to scale, embodying the principles of the present invention.

A needle assembly, shown in FIG. 1 embodying the principles of the present invention, includes a stationary housing 10 having a chamber 12 therein. The chamber 12 communicates, via a port 14, with a carrier gas conduit 16 adapted to be shut off, and a separating column 18 (FIG. 3). A needle 20 having a tip 22 is guided in the housing 10 in sealing means for sliding movement between a position of rest and an operating position. The needle 20 includes a first lateral opening 24 (FIG. 2) close to the tip 22 and a second lateral opening 26 spaced from the first lateral opening 24. The two openings, 24 and 26, are interconnected by a longitudinal passage 28 of the needle 20. At the lower end, as viewed is a FIG. 5, the passage 28 is closed by an end piece 30 forming the tip 22. Above the second opening 26, the passage 28 is closed by a solid upper end piece 32. In the operating position, which is designated as "position 2" in FIG. 4, the second lateral opening 26 communicates with the chamber 12 such that a carrier gas flows through the second opening 26 into the needle 20 and out of the first opening 24.

The needle 20 is movable relative to the stationary housing 10 by, for example, a servomotor 34 between the position of rest, illustrated in FIGS. 1 and 3 (position 1 in FIG. 2) and the operating position (position 2 in FIG. 4). The housing 10 includes a longitudinal passage defining the chamber 12, the wall of which surrounds the needle 20 leaving free a narrow annular gap therebetween. The longitudinal passage 28 has a first end adjacent the tip 22 of the needle 20, which end is the lower one in FIG. 1 and a second end, remote from the tip 22, the upper one in FIG. 1. The sealing means includes a pair of seals 36 and 38, provided in the area of the first end of the longitudinal passage 28 axially spaced from each other and closely engaging the needle 20. In the area of the second end of the longitudinal passage 28, a seal 40 is provided which closely engages the needle 20. The port 14 for the carrier gas conduit 16 terminates at the first end axially inwards of the seals 36 and 38. The needle 20 is movable by the servomotor 34 into the position of rest (position 1) in which the first lateral opening 24 on the first end is located between the pair of seals 36 and 38; and into the operating position (position 2) in which the needle 20 with its tip and the first lateral opening 24 extends out of the housing 10 and the second lateral opening 26 is arranged beside the port 14 for the carrier gas conduit 16. A port 42 connected to atmosphere is provided at the second end axially inwards of the seal 40.

In one preferred embodiment, the chamber 12 is formed by a sleeve 44. The sleeve 44 is positioned in a dosing head 46 having an insulated heater 48 vulcanized thereon. By means of the heater 48, the temperature of the dosing head 46 is regulated, for example, between 30° C. and 100° C. The sealing means by which the chamber 12 is sealed includes a first head piece 50 which engages the end face of the first, in FIG. 1 lower end of the sleeve 44. The pair of seals, 36 and 38, provided near the first end of the sleeve 44 is supported in the head piece 50. The second pair of seals, 36 and 38, is formed by O-rings located in annular grooves of the head piece 50. The O-rings are preferably formed from a fluorosilicon material and rubbed in graphite powder to reduce friction. The sealing means furthermore has a second head piece 54, preferably formed of a synthetic plastic, which engages the end face of the second, in FIG. 1, end of the sleeve 44 and has an aperture 56 in alignment with the longitudinal passage 28 of the sleeve 44. The seal 40 provided near the second end of the sleeve 44 is supported in the second head piece. In addition, the seal 40 is formed by an O-ring positioned in an annular groove in the aperture 56, which O-ring is formed from a fluorosilicon material and rubbed in graphite powder. The synthetic plastic rings, 58 and 60 respectively, are aligned with the apertures, 52 and 56, in the head pieces 50 and 54. The needle 20 is longitudinally movably guided in the synthetic plastics rings, 58 and 60. In this way, the functions of guiding and axial sealing are separated from each other. At least one of the synthetic plastics rings, in the preferred embodiment the synthetic ring 58, is made from a chemically resistant synthetic plastic. It is arranged on the side of the associated O-rings 36 and 38 facing the chamber 12. Thus, the O-rings are substantially protected against the influences of aggressive components which may be present in the sample gas.

The head piece 50 at the first end of the sleeve 44 is located in a recess 62 of the dosing head 46 and sealingly engages the bottom of the recess 62 and the end face of the sleeve 44 is essentially aligned therewith. The recess 62 includes an internal thread 64 whereby a nut 68, provided with a central aperture 66 aligned with the longitudinal passage of the sleeve 44, is screwed. The nut 68 urges the head piece 50 against the bottom of the recess 62 and the end face of the sleeve 44. The dosing head 46 has a transverse slot 70 lateral to the head piece 50 and intersecting the recess 62 receiving the head piece 50. The needle 20 is adapted to be moved back by the servomotor 34 into a position whereat the tip 22 is located completely within the sleeve 44. The head piece 50 can then be removed laterally through the slot 70, after the nut 68 has been released, or a head piece 50 can be set in through the slot 70. Such an arrangement permits the easy changing of the head piece 50 which wears in operation and therefore occasionally requires replacement.

An externally threaded projection 72 is provided on the dosing head 46 about the second end of the sleeve 44 and coaxial thereto. A body 74 having a longitudinal passage 76 for the needle 20 and an internally threaded cylindrical recess 78, with which it extends over the projection 72, is screwed on this projection, the internal thread of the body 74 being screwed on the external thread of the projection 72. The head piece 54 located at the second end of the sleeve 44 is held between the bottom of the recess 78 of this body 74 and the end faces of the sleeve 44 and of the projection 72 and is pressed against the latter ones. A spring washer, for example a cup spring 80, is arranged between the bottom of the recess 78 and the head piece 72. This cup spring 80 compensates for modifications in the dimensions of the head piece 54 caused by the flowing of the synthetic plastic.

Figure 5:
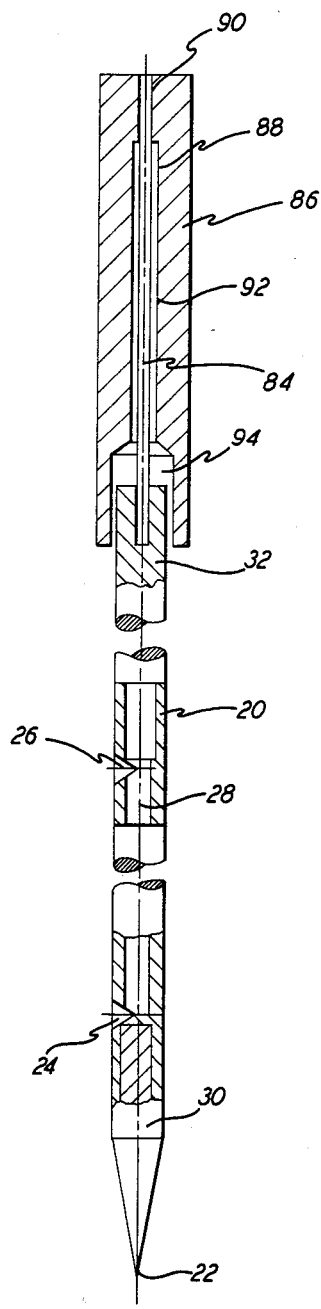
FIG. 5 illustrates the needle of the present invention in greater detail than the other figures.

At the end remote from the tip 22, the needle 20 is connected to a displacement member 82 movable by the servomotor 34 through an intermediate spring member 84 (FIG. 5) permitting a compensation of tolerances between guide and drive of the needle 20. As can be seen in FIG. 5, a longitudinal, cylindrical clamping head 86 is provided with a stepped longitudinal bore 88. The intermediate spring member 84 is clamped in the narrowest portion 90 of this longitudinal bore at one end of the clamping head 86. The intermediate spring member then extends through a median section 92 of the longitudinal bore having a larger diameter and therefore permits lateral movement of the intermediate spring member 84. At the free end, the intermediate spring member 84 is connected to the solid section 32 on the end of the needle 20 opposite the tip 22. An enlarged third section 94 of the longitudinal bore 88 extends over this end of the needle 20. The clamping head 86 is located in a recess on the end face of the displacement member 82 and is held by a cap nut 96. The displacement member 82 with which the needle 20 is connected is a rack longitudinally movably guided in alignment with the longitudinal passage of the sleeve 44. The rack meshes with a pinion 98 which is driven by servomotor 34. A code disk 100 which is arranged to be picked-up by a pick-up head, i.e., a light barrier 102, is connected to the pinion 98 for monitoring and controlling the servomotor. In one embodiment, a pot-shaped housing projection 104 passing into the guide of the rack 82 and extending over the body 44 is provided on the motor 34. In this way, good alignment of the rack 82 and the sleeve 44 as well as the needle 20 is assured. Tolerances are compensated for by the intermediate spring member 84. The body 74 is surrounded by an insulating jacket 106.

As shown in FIG. 3, the port 14 is on one hand, connected to the carrier gas conduit including a pressure regulator 108 and a solenoid valve 110. On the other hand, the separating column 18 is connected to the port 14 through a conduit 112. The port 42 is connected to atmosphere via a solenoid valve 114 and a flow restrictor 116.

As can be seen from FIG. 4, the needle 20, under the control of the servomotor, is movable into a third position (stand-by position) designated by "position 3" in FIG. 4.

In this third position, the second lateral opening 26 is located between the two seals 36 and 38, provided at the first end of the longitudinal passage 28. Furthermore, the needle is movable by the servomotor 34 into a fourth position (venting position) designated as "position 4". In this fourth position, the second lateral opening is located axially outwards of the two seals, 36 and 38, provided at the first end of the longitudinal passage and is connected to the atmosphere. If a sample vessel 118 is located below the needle 20 such as indicated in FIG. 2, then the longitudinal passage 28 of the needle 20 communicates, via the first lateral opening 24, with the inner portion of the sample vessel 118, while the second lateral opening 26 is sealingly closed by the two seals 36 and 38. Therefore, no gas can escape from the sample vessel 118. The carrier gas flow flows as a rinsing flow from the port 14 through the chamber 12 to the port 42 and out to the atmosphere.

In the fourth position of the needle, the second lateral opening 26 communicates with the atmosphere. Sample gas can now escape into atmosphere whereby the pressure is equalized in the sample vessel 118. This permits the method of "gas extraction", with which several samples are taken and the sample vessel is vented respectively in the meantime.

The needle 20, under the control of the servomotor 34, is also movable into a fifth position (back-flush position), which is designated in FIG. 4 as "position 5". In this fifth position, the first lateral opening 24 is located axially closely outwards of the two seals, 36 and 38, provided at the first end of the longitudinal passage 12 on one hand and the seal 40 on the other hand. Thus, there is gaseous communication within the chamber 12 between the seals. Carrier gas is then passed from the separating column through the inlet of the separating column to atmosphere as a back-flush operation. This is carried out in a known manner with inversion of the flow direction through the separating column with certain not easily volatilized components of the sample being flushed back from the separating column. During this method of operation, the needle 20, in combination with the seals 36, 38 and 40, acts as a slide valve.

Although the present invention has been described herein by means of an exemplary embodiment, other configurations and arrangements which do not depart from the spirit and scope of the present invention will become apparent to those skilled in the art. Consequently, the present invention is deemed limited only by the appended claims and the reasonable interpretation thereof.

What is claimed is:

1. Needle assembly useful as a sampling device in gas chromatography operating with the head space method; said assembly comprises:
   a stationary housing having a chamber therein; said chamber defining a longitudinal passage;
   a needle having a tip; said needle being sealingly guided in said longitudinal passage and defining a narrow annular gap therebetween, said longitudinal passage having a first end proximate said tip of said needle and a second end distal therefrom; said needle having a first lateral opening proximate said tip and a second lateral opening distal therefrom;
   a pair of seals proximate said end of said longitudinal passage, said seals being spaced apart and closely engaging said needle;
   a separate seal proximate said second end of said longitudinal passage and closely engaging said needle;
   a first port communicating with a carrier gas conduit and terminating at said chamber between said pair of seals and said separate seal, said conduit being adapted to be shut off; said port being switchably connectable with a separating column; and
   a servomotor for moving said needle between a position of rest and an operating position relative to said stationary housing whereby at said position of rest said first lateral opening is between said pair of seals and whereby at said operating position said needle, tip and said first lateral opening extend out of said housing and said second lateral opening is in gaseous communication with said first port whereby a carrier gas can pass through said second opening into said needle and out of said first lateral opening.

2. Needle assembly as claimed in claim 1, further comprising:
   a second port, said second port being connectable to atmosphere and communicating with said second end of said passage.

3. Needle assembly as claimed in claim 2, wherein said needle, is movable, via said servomotor into a stand-by position, whereat said second lateral opening is between said pair of seals provided at said first end of said longitudinal passage, and a venting position, whereat said second lateral opening is located axially outwards of said pair of seals and in gaseous communication with atmosphere.

4. Needle assembly as claimed in claim 2, wherein said needle is movable into a back-flush position whereat said first lateral opening is located axialy closely outwards of said pair of seals and in communication with atmosphere and said second lateral open is between said pair of seals on one hand and said seal at the other end of said longitudinal passage on the other hand and communicates with chamber.

5. Needle assembly as claimed in claim 4 wherein said longitudinal passage is defined by a sleeve.

6. Needle assembly as claimed in claim 5, wherein said sealing means including;
 a first head piece of synthetic plastics engaging the end face of a first end of said sleeve and an aperture aligned with said longitudinal passage of said sleeve in which said pair of seals is supported; and
 a second head piece of synthetic plastics, engaging the end face of a second end of said sleeve and an aperture aligned with said longitudinal passage of said sleeve and in which said separate seal is supported.

7. Needle assembly as claimed in claim 6, wherein: said seals are formed by O-rings located in annular grooves in said apertures of said head pieces.

8. Needle assembly as claimed in claim 7, wherein: said O-rings are a fluorosilicon material and are rubbed in graphite powder to reduce the friction.

9. Needle assembly as claimed in claim 8, wherein: said synthetic plastics rings are aligned with said aperture in said head pieces; and
 said needle is longitudinally movably guided in these synthetic plastics rings.

10. Needle assembly as claimed in claim 9, wherein at least one of said synthetic plastics rings is a chemically highly resistant synthetic plastics and is arranged on the side of the associated O-ring facing said chamber.

11. Needle assembly as claimed in claim 5, wherein: said sleeve is positioned in a heated dosing head, said head piece at said first end of said sleeve being located in a recess of said dosing head such that it sealingly engages the bottom of a recess and the end face of the sleeve essentially aligned therewith, said recess having an internal thread on which a nut is screwed, said nut being provided with a central aperture aligned with said longitudinal passage of said sleeve and, which nut urges said head piece against said bottom of said recess and said end face of said sleeve.

12. Needle assembly as claimed in claim 11, wherein: said dosing head, laterally of said head piece includes a transverse slot intersecting said recess receiving said head piece, and said needle, being movable into a position at which said tip of said needle is completely within said sleeve whereby, after said nut has been released, said head piece can be removed or inserted, laterally through said slot.

13. Needle assembly as claimed in claim 12, further including:
 an externally threaded projection being provided at said dosing head about said second end of said sleeve and coaxial therewith;
 a body is screwed on this projection, said body having a longitudinal passage for said needle and an internally threaded cylindrical recess with which it extends over the projection, said internal thread of said body being screwed on said external thread of said projection; and
 said head piece being located at said second end of said sleeve is retained between said bottom and said end faces of said sleeve and of said projection and is urged against the latter ones.

14. Needle assembly as claimed in claim 13, wherein: a spring washer is arranged between said bottom of said recess and said head piece.

15. Needle assembly as claimed in claim 5 wherein: said needle being connected to a rack longitudinally movably guided in alignment with said longitudinal passage of said sleeve, said rack meshing with a pinion driven by said servomotor.

16. Needle assembly as claimed in claim 15, further including:
 a code disc, arranged to be picked-up by a light barrier pick-up head, said code disc being connected to said pinion for monitoring and controlling said servomotor.

17. Needle assembly as claimed in claim 2 wherein: said needle being connected, at its end opposite said tip, to a displacement member movable by said servomotor through an intermediate spring member permitting compensation of tolerances between guide and drive of said needle.

* * * * *